US011103205B2

(12) United States Patent
O'Dea et al.

(10) Patent No.: US 11,103,205 B2
(45) Date of Patent: Aug. 31, 2021

(54) BEDSIDE DYNAMIC IMAGING

(71) Applicant: CARESTREAM HEALTH, INC., Rochester, NY (US)

(72) Inventors: Dennis J. O'Dea, Farmington, NY (US); Xiaohui Wang, Pittsford, NY (US); Samuel Richard, Rochester, NY (US); Michael Ficarra, Pittsford, NY (US); Joseph E. Stagnitto, Conesus, NY (US); Michael C. Lalena, Webster, NY (US); Kenneth J. Brown, Fairport, NY (US)

(73) Assignee: Carestream Health, Inc., Rochester, NY (US)

(*) Notice: Subject to any disclaimer, the term of this patent is extended or adjusted under 35 U.S.C. 154(b) by 108 days.

(21) Appl. No.: 16/487,130

(22) PCT Filed: Mar. 26, 2018

(86) PCT No.: PCT/US2018/024274
§ 371 (c)(1),
(2) Date: Aug. 20, 2019

(87) PCT Pub. No.: WO2018/183160
PCT Pub. Date: Oct. 4, 2018

(65) Prior Publication Data
US 2021/0137477 A1    May 13, 2021

Related U.S. Application Data

(60) Provisional application No. 62/477,032, filed on Mar. 27, 2017.

(51) Int. Cl.
*A61B 6/00* (2006.01)
*A61B 6/06* (2006.01)
*G01T 1/20* (2006.01)

(52) U.S. Cl.
CPC ............ *A61B 6/487* (2013.01); *A61B 6/06* (2013.01); *A61B 6/4233* (2013.01);
(Continued)

(58) Field of Classification Search
CPC ......... A61B 6/06; A61B 6/488; A61B 6/4085; A61B 6/4405; A61B 6/4411; A61B 6/487; A61B 6/547; A61B 6/4441; A61B 6/464
See application file for complete search history.

(56) References Cited

U.S. PATENT DOCUMENTS 9,788,810 B2 * 10/2017 Ancar ................ A61B 6/542
2007/0041508 A1    2/2007 Tubbs
(Continued)

OTHER PUBLICATIONS

International Search Report dated Sep. 4, 2018 for International Application No. PCT/US2018/024274, 2 Pages.

*Primary Examiner* — Don K Wong

(57) ABSTRACT

A method of operating a mobile fluoroscopic imaging system includes positioning an x-ray source and a DR detector about a patient. Data defining a spatial configuration of the x-ray source and the collimator is stored in the system. The system is configured to determine a source-to-image distance of the x-ray source and the DR detector including by activating the x-ray source and capturing a scout image in the DR detector. Dimensions of the scout image are calculated and the source-to-image distance is determined based on the data defining the spatial configuration of the x-ray source and the collimator and on the dimensions of the scout image.

16 Claims, 9 Drawing Sheets

(52) U.S. Cl.
CPC ............ *A61B 6/4405* (2013.01); *A61B 6/488* (2013.01); *A61B 6/587* (2013.01); *A61B 6/588* (2013.01); *G01T 1/2018* (2013.01)

(56) References Cited

U.S. PATENT DOCUMENTS

| | | |
|---|---|---|
| 2012/0230473 A1 | 9/2012 | Stagnitto et al. |
| 2015/0223767 A1 | 8/2015 | Sehnert et al. |
| 2015/0366525 A1* | 12/2015 | Sandholm ............ A61B 6/5264 378/4 |
| 2015/0374314 A1* | 12/2015 | Maack ................... A61B 6/588 378/62 |

\* cited by examiner

BEDSIDE DYNAMIC IMAGING

CROSS REFERENCE TO RELATED APPLICATIONS

This application claims the benefit of and is a U.S. National Phase filing of PCT Application PCT/US2018/024274 filed Mar. 26, 2018 entitled "BEDSIDE DYNAMIC IMAGING", in the name of Dennis J. O'Dea et al., which claims benefit of U.S. Patent Application Ser. No. 62/477,032, filed Mar. 27, 2017, in the name of Dennis J. O'Dea et al., and entitled BEDSIDE DYNAMIC IMAGING.

BACKGROUND OF THE INVENTION

The subject matter disclosed herein relates to mobile digital radiographic imaging systems utilizing manually positioned digital radiographic (DR) detectors. More specifically, the invention relates to methods and apparatus for assisting in determining alignment of the x-ray source and the DR detector.

Some bedside dynamic imaging (fluoroscopy) systems use a multi-positionable tube head and portable detector that are not rigidly attached to each other. Methods and apparatuses for determining alignment and sizing of the collimation area in such systems are disclosed herein.

When an x-ray image is obtained, there is generally an optimal distance and angle between the radiation source and the two dimensional DR detector that records the image data. In most cases, it is preferred that the x-ray source provide radiation in a direction that is generally perpendicular to the surface of the DR detector. For this reason, large-scale radiography systems mount the radiation head and the DR detector holder at a specific angle relative to each other. Orienting the radiation head and the DR detector typically requires a C-arm of substantial size, extending outward well beyond the full distance between these two components. With such large-scale systems, source-to-image distance (SID) is tightly controlled and unwanted tilt or skew of the DR detector is thus prevented by the hardware of the imaging system itself. Further, because the spatial positioning and geometry of conventional large-scale systems is well-controlled, proper alignment of the x-ray source and DR detector is straightforward.

Mobile x-ray apparatuses are of particular value in intensive care unit (ICU) and other environments where timely acquisition of a radiographic image is important. Because it can be manually wheeled around the ICU or other area and brought directly to the patient's bedside, a mobile x-ray system allows an attending physician or clinician to have recent information on the condition of a patient and helps to reduce the risks entailed in moving patients to stationary equipment in the radiological facility. With the advent of mobile radiation imaging systems, such as those used in Intensive Care Unit (ICU) environments, a fixed angular relationship between the radiation source and two-dimensional DR detector, and accompanying grid, if any, is no longer maintained by the mounting hardware of the system itself. Instead, an operator is required to aim the radiation source toward the DR detector imaging surface, providing as perpendicular an orientation as possible, typically using a visual assessment. The DR detector itself, however, may not be visible to the technician once it is positioned underneath or behind the patient. This complicates the alignment task for mobile systems, requiring some method and apparatus for measuring SID and tilt angle, and making it more difficult to use a grid effectively for reducing the effects of radiation scatter.

There have been a number of approaches to the problem of providing methods and tools to assist operator adjustment of x-ray source-to-DR detector angle. Some approaches are described in U.S. Pat. No. 8,827,554 entitled "Tube Alignment for Mobile Radiography System" to Lalena et al., which is hereby incorporated by reference herein in its entirety. Other approaches project a light beam from the radiation source to the DR detector in order to achieve alignment between the two. Examples of this approach include U.S. Pat. No. 5,388,143 entitled "Alignment Method for Radiography and Radiography Apparatus Incorporating Same" and U.S. Pat. No. 5,241,578 entitled "Optical Grid Alignment System for Portable Radiography and Portable Radiography Apparatus Incorporating Same", both to MacMahon. Similarly, U.S. Pat. No. 6,154,522 entitled "Method, System and Apparatus for Aiming a Device Emitting Radiant Beam" to Cumings describes the use of a reflected laser beam for alignment of the radiation target. However, the solutions that have been presented using light to align the film or CR cassette or DR detector are constrained by a number of factors. The '143 and '578 MacMahon disclosures require that a fixed Source-to-Image Distance (SID) be determined beforehand, then apply triangulation with this fixed SID value. Changing the SID requires a number of adjustments to the triangulation settings. This arrangement is less than desirable for portable imaging systems that allow a variable SID. Devices using lasers, such as that described in the '522 Cumings disclosure, in some cases can require much more precision in making adjustments than is necessary.

Today's portable radiation imaging systems allow considerable flexibility for placement of the DR detector by the radiology technician. The patient need not be in a horizontal position for imaging, but may be at any angle, depending on the type of image that is needed and on the ability to move the patient for the x-ray examination. The technician can manually adjust the position of both the DR detector and the radiation source independently for each imaging session. Thus, it can be appreciated that a system for determining SID and angle between the radiation source and the DR detector must be able to adapt to whatever orientation is best suited for obtaining a particular radiographic image.

The discussion above is merely provided for general background information and is not intended to be used as an aid in determining the scope of the claimed subject matter.

BRIEF DESCRIPTION OF THE INVENTION

A method of operating a mobile fluoroscopic imaging system is disclosed wherein an x-ray source and a DR detector are manually positioned about a patient. Data defining a spatial configuration of the x-ray source and the collimator is stored in the system. The system is configured to determine a source-to-image distance of the x-ray source and the DR detector by activating the x-ray source and capturing a scout image in the DR detector. Dimensions of the scout image are calculated and the source-to-image distance is determined based on the data defining the spatial configuration of the x-ray source and the collimator and on the dimensions of the scout image.

In one embodiment a method of operating a mobile fluoroscopic imaging system includes positioning an x-ray source and a DR detector about a patient. Data defining a spatial configuration of the x-ray source and the collimator is stored in the system. The system is configured to determine a source-to-image distance of the x-ray source and the DR detector including by activating the x-ray source and capturing a scout image in the DR detector. Dimensions of the scout image are calculated and the source-to-image distance is determined based on the data defining the spatial configuration of the x-ray source and the collimator and on the dimensions of the scout image.

In another embodiment, a method of operating a mobile fluoroscopic imaging system having a mounted x-ray source, a collimator, and a freely positionable DR detector includes positioning the x-ray source and the DR detector about a patient. Inclinometers are provided on the x-ray source and the detector to determine that the x-ray source and the detector are parallel within an acceptable tolerance. An aperture of the collimator is set to a preselected size and a scout image is captured on the DR detector. A size of the radiation field of the scout image on the DR detector is determined and increased aperture size is calculated so that the radiation field of the increased aperture size fits within borders of the DR detector. The aperture is set to the increased size and a fluoroscopic examination is commenced.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

This application claims priority to U.S. Patent Application Ser. No. 62/477,032, filed Mar. 27, 2017, in the name of O'Dea et al., and entitled BEDSIDE DYNAMIC IMAGING, which is hereby incorporated by reference herein in its entirety.

Figure 1:
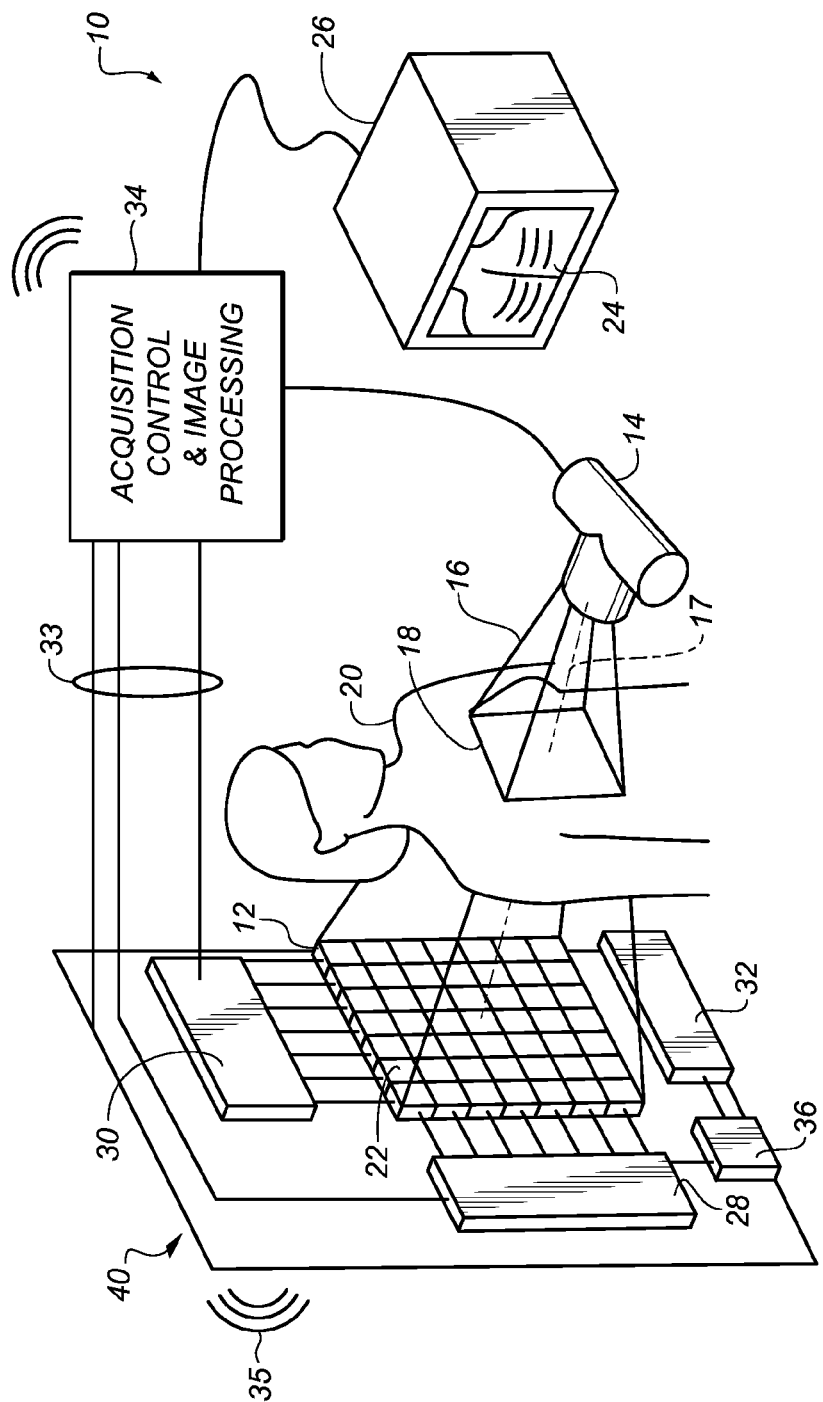
FIG. 1 is a schematic perspective view of an exemplary x-ray system.

FIG. 1 is a perspective view of a digital radiographic (DR) imaging system 10 that may include a generally curved or planar DR detector 40 (shown in a planar embodiment and without a housing for clarity of description), an x-ray source 14 configured to generate radiographic energy (x-ray radiation), and a digital monitor, or electronic display, 26 configured to display images captured by the DR detector 40, according to one embodiment. The DR detector 40 may include a two dimensional array 12 of detector cells 22 (photosensors), arranged in electronically addressable rows and columns. The DR detector 40 may be positioned to receive x-rays 16 passing through a subject 20 during a radiographic imaging session as emitted by the x-ray source 14. As shown in FIG. 1, the radiographic imaging system 10 may use an x-ray source 14 that emits collimated x-rays 16, e.g. an x-ray beam, selectively aimed at and passing through a preselected region 18 of the subject 20. The x-ray beam 16 may be attenuated by varying degrees along its plurality of rays according to the internal structure of the subject 20, which attenuated rays are detected by the two-dimensional array 12 of photosensitive detector cells 22. The curved or planar DR detector 40 is positioned, as much as possible, in a perpendicular relation to a substantially central ray 17 of the plurality of rays 16 emitted by the x-ray source 14. In a curved array embodiment, the source 14 may be centrally positioned such that a larger percentage, or all, of the photosensitive detector cells are positioned perpendicular to incoming x-rays from the centrally positioned source 14. The array 12 of individual photosensitive cells (pixels) 22 may be electronically addressed (scanned) by their position according to column and row. The location of particular pixels may be recorded according to column and row as described herein, in order to determine a distance between selected ones of the pixels. In particular, pixels which transition, or change state, to a charged state as a result of receiving x-ray radiation may be recorded, by column and row, as being located within a collimated radiation field while those pixels which do not transition to a charged state are known to not be impacted by x-ray radiation.

The density of pixels in a particular DR detector is known, thus, two row×column rectilinear indexes each associated with one of two pixels may be used to determine a distance between the two pixels using simple trigonometric calculations. As used herein, the terms "column" and "row" refer to the vertical and horizontal arrangement of the photosensor cells 22 and, for clarity of description, it will be assumed that the rows extend horizontally and the columns extend vertically. However, the orientation of the columns and rows is arbitrary and does not limit the scope of any embodiments disclosed herein. Furthermore, the term "subject" may be illustrated as a human patient in the description of FIG. 1, however, a subject of a DR imaging system, as the term is used herein, may be a human, an animal, or a portion thereof.

In one exemplary embodiment, the rows of photosensitive cells 22 may be scanned one or more at a time by electronic scanning circuit 28 so that the exposure data from the array 12 may be transmitted to electronic read-out circuit 30. Each photosensitive cell 22 may independently store a charge proportional to an intensity, or energy level, of the attenuated radiographic radiation, or x-rays, received and absorbed in the cell. Particular pixels of the array may be selected and identified by a row×column index for having absorbed a particular amount of radiographic energy to transition to a charged state, such as a high intensity and energy level. Furthermore, each photosensitive cell, when read-out, provides information defining a pixel of a radiographic image 24, e.g. a brightness level or an amount of energy absorbed by the pixel, that may be digitally decoded by image processing electronics 34 and transmitted to be displayed by the digital monitor 26 for viewing by a user. An electronic bias circuit 32 is electrically connected to the two-dimensional detector array 12 to provide a bias voltage to each of the photosensitive cells 22.

Each of the bias circuit 32, the scanning circuit 28, and the read-out circuit 30, may communicate with an acquisition control and image processing unit 34 over a connected cable 33 (wired), or the DR detector 40 and the acquisition control and image processing unit 34 may be equipped with a wireless transmitter and DR detector to transmit radiographic image data wirelessly 35 to the acquisition control and image processing unit 34. The acquisition control and image processing unit 34 may include a processor and electronic memory (not shown) to control operations of the DR detector 40 as described herein, including control of circuits 28, 30, and 32, for example, by use of programmed instructions, and to store and process image data. The acquisition control and image processing unit 34 may also be used to control activation of the x-ray source 14 during a radiographic exposure, controlling an x-ray tube electric current magnitude, and thus the fluence of x-rays in x-ray beam 16, and/or the x-ray tube voltage, and thus the energy level of the x-rays in x-ray beam 16. The acquisition control and image processing unit 34 may also be used to selectively identify pixels in the array by a row×column index for having absorbed a particular amount of radiographic energy and to record these indices to be used for source-to-image distance and detector angular tilt calculations, as described herein. A portion or all of the acquisition control and image processing unit 34 functions may reside in the detector 40 in an on-board processing system 36 which may include a processor and electronic memory to control operations of the DR detector 40 as described herein, including control of circuits 28, 30, and 32, by use of programmed instructions, and to store and process image data similar to the functions of standalone acquisition control and image processing system 34. The image processing system may perform image acquisition and image disposition functions as described herein. The image processing system 36 may control image transmission and image processing and image correction on board the detector 40 based on instructions or other commands transmitted from the acquisition control and image processing unit 34, and transmit corrected digital image data therefrom. Alternatively, acquisition control and image processing unit 34 may receive raw image data from the detector 40 and process the image data and store it, or it may store raw unprocessed image data in local memory, or in remotely accessible memory.

With regard to a direct detection embodiment of DR detector 40, the photosensitive cells 22 may each include a sensing element sensitive to x-rays, i.e. it absorbs x-rays and generates an amount of charge carriers in proportion to a magnitude of the absorbed x-ray energy. A switching element may be configured to be selectively activated to read out the charge level of a corresponding x-ray sensing element. With regard to an indirect detection embodiment of DR detector 40, photosensitive cells 22 may each include a sensing element sensitive to light rays in the visible spectrum, i.e. it absorbs light rays and generates an amount of charge carriers in proportion to a magnitude of the absorbed light energy, and a switching element that is selectively activated to read the charge level of the corresponding sensing element. A scintillator, or wavelength converter, may be disposed over the light sensitive sensing elements to convert incident x-ray radiographic energy to visible light energy. Thus, in the embodiments disclosed herein, it should be noted that the DR detector 40 may include an indirect or direct type of DR detector.

Examples of sensing elements used in sensing array 12 include various types of photoelectric conversion devices (e.g., photosensors) such as photodiodes (P-N or PIN diodes), photo-capacitors (MIS), photo-transistors or photoconductors. Examples of switching elements used for signal read-out include a-Si TFTs, oxide TFTs, MOS transistors, bipolar transistors and other p-n junction components.

Figure 2:
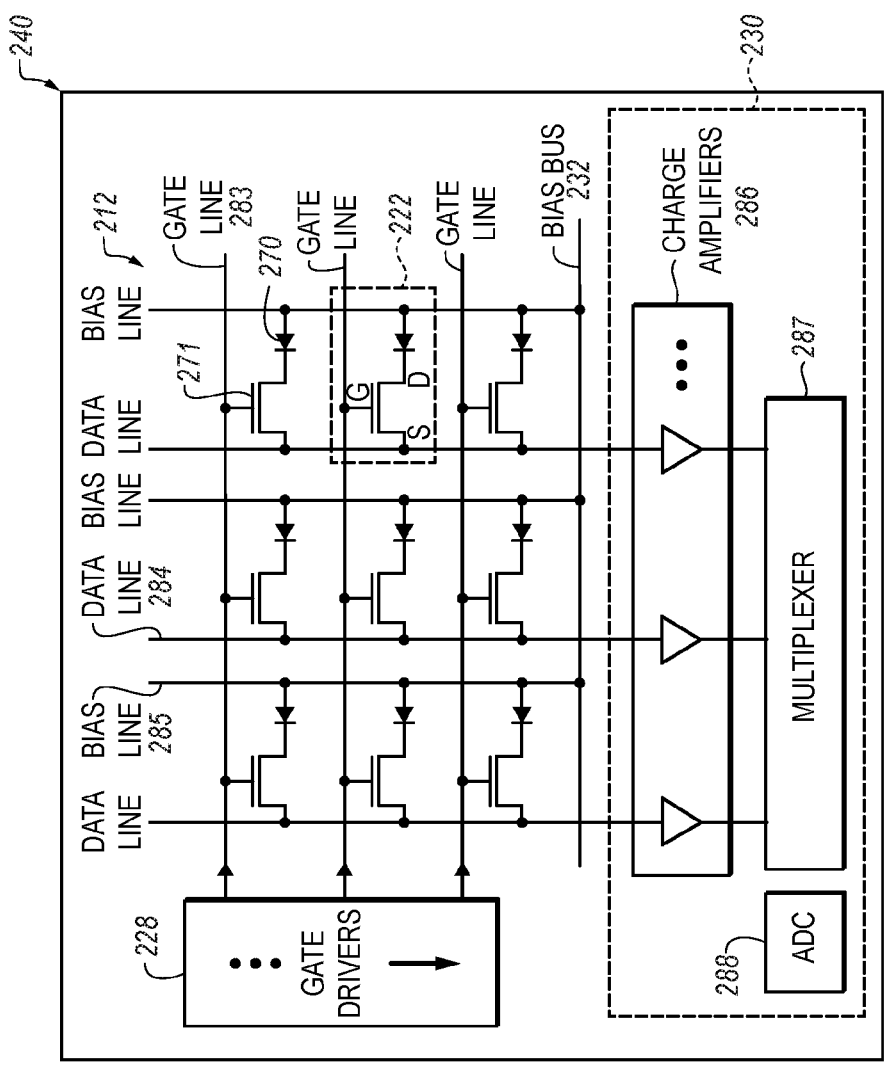
FIG. 2 is a schematic diagram of a photosensor array in a radiographic detector.

FIG. 2 is a schematic diagram 240 of a portion of a two-dimensional array 12 of photosensitive cells 222 for a DR detector 40. The array of photosensor cells 212, whose operation may be consistent with the photosensor array 12 described above, may include a number of hydrogenated amorphous silicon (a-Si:H) n-i-p photodiodes 270 and thin film transistors (TFTs) 271 formed as field effect transistors (FETs) each having gate (G), source (S), and drain (D) terminals. In embodiments of DR detector 40 disclosed herein, the two-dimensional array of photosensor cells 12 may be formed in a device layer that abuts adjacent layers of the DR detector structure, which adjacent layers may include a rigid glass layer or a flexible polyimide layer or a layer including carbon fiber without any adjacent rigid layers. A plurality of gate driver circuits 228 may be electrically connected to a plurality of gate lines 283 which control a voltage applied to the gates of TFTs 271, a plurality of readout circuits 230 may be electrically connected to data lines 284, and a plurality of bias lines 285 may be electrically connected to a bias line bus or a variable bias reference voltage line 232 which controls a voltage applied to the photodiodes 270. Charge amplifiers 286 may be electrically connected to the data lines 284 to receive signals therefrom. Outputs from the charge amplifiers 286 may be electrically connected to a multiplexer 287, such as an analog multiplexer, then to an analog-to-digital converter (ADC) 288, or they may be directly connected to the ADC, to stream out the digital radiographic image data at desired rates. In one embodiment, the schematic diagram of FIG. 2 may represent a portion of a DR detector 40 such as an a-Si:H based indirect flat panel, curved panel, or flexible panel imager.

Incident x-rays, or x-ray photons, 16 are converted to optical photons, or light rays, by a scintillator, which light rays are subsequently converted to electron-hole pairs, or charges, upon impacting the a-Si:H n-i-p photodiodes 270. In one embodiment, an exemplary detector cell 222, which may be equivalently referred to herein as a pixel, may include a photodiode 270 having its anode electrically connected to a bias line 285 and its cathode electrically connected to the drain (D) of TFT 271. The bias reference voltage line 232 can control a bias voltage of the photodiodes 270 at each of the detector cells 222. The charge capacity of each of the photodiodes 270 is a function of its bias voltage and its capacitance. In general, a reverse bias voltage, e.g. a negative voltage, may be applied to the bias lines 285 to create an electric field (and hence a depletion region) across the pn junction of each of the photodiodes 270 to enhance its collection efficiency for the charges generated by incident light rays. The image signal represented by the array of photosensor cells 212 may be integrated by the photodiodes while their associated TFTs 271 are held in a non-conducting (off) state, for example, by maintaining the gate lines 283 at a negative voltage via the gate driver circuits 228. The photosensor cell array 212 may be read out by sequentially switching rows of the TFTs 271 to a conducting (on) state by means of the gate driver circuits 228. When a row of the pixels 22 is switched to a conducting state, for example by applying a positive voltage to the corresponding gate line 283, collected charge from the photodiode in those pixels may be transferred along data lines 284 and integrated by the external charge amplifier circuits 286. The row may then be switched back to a non-conducting state, and the process is repeated for each row until the entire array of photosensor cells 212 has been read out. The integrated signal outputs are transferred from the external charge amplifiers 286 to an analog-to-digital converter (ADC) 288 using a parallel-to-serial converter, such as multiplexer 287, which together comprise read-out circuit 230.

This digital image information may be subsequently processed by image processing system 34 to yield a digital image which may then be digitally stored and immediately displayed on monitor 26, or it may be displayed at a later time by accessing the digital electronic memory containing the stored image. The flat panel DR detector 40 having an imaging array as described with reference to FIG. 2 is capable of both single-shot (e.g., static, radiographic) and continuous, e.g., fluoroscopic, image acquisition, which may be referred to herein as serial radiographic image acquisition.

Figure 3:
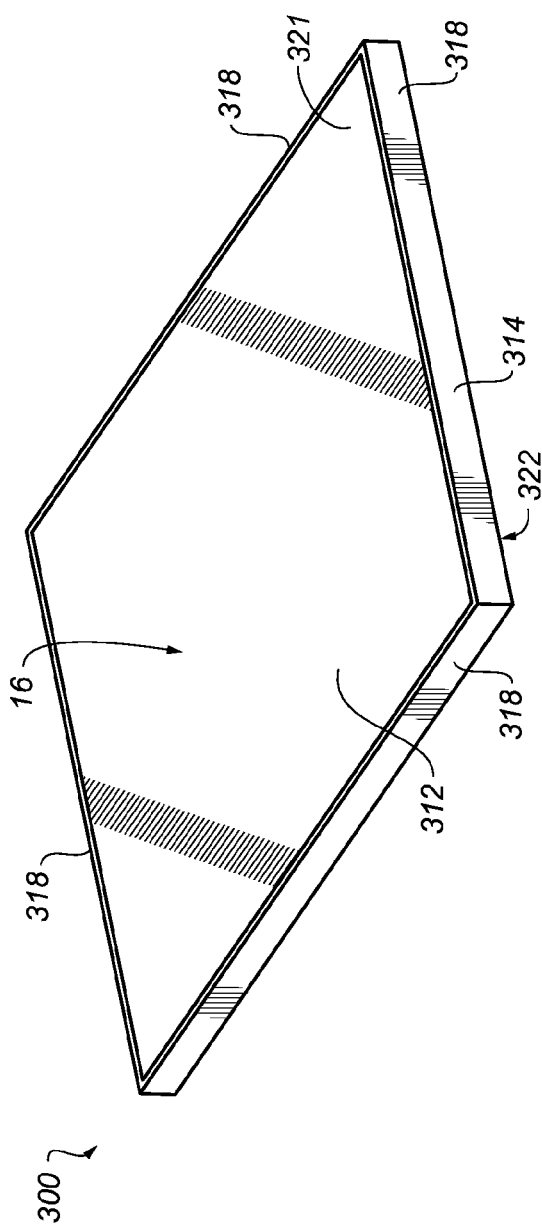
FIG. 3 is a perspective diagram of an exemplary DR detector.

FIG. 3 shows a perspective view of an exemplary prior art generally rectangular, planar, portable wireless DR detector 300 according to an embodiment of DR detector 40 disclosed herein. The DR detector 300 may include a flexible substrate to allow the DR detector to capture radiographic images in a curved orientation. The flexible substrate may be fabricated in a permanent curved orientation, or it may remain flexible throughout its life to provide an adjustable curvature in two or three dimensions, as desired. The DR detector 300 may include a similarly flexible housing portion 314 that surrounds a multilayer structure comprising a flexible photosensor array portion 22 of the DR detector 300. The housing portion 314 of the DR detector 300 may include a continuous, rigid or flexible, x-ray opaque material or, as used synonymously herein a radio-opaque material, surrounding an interior volume of the DR detector 300. The housing portion 314 may include four flexible edges 318, extending between the top side 321 and the bottom side 322, and arranged substantially orthogonally in relation to the top and bottom sides 321, 322. The bottom side 322 may be continuous with the four edges and disposed opposite the top side 321 of the DR detector 300. The top side 321 comprises a top cover 312 attached to the housing portion 314 which, together with the housing portion 314, substantially encloses the multilayer structure in the interior volume of the DR detector 300. The top cover 312 may be attached to the housing 314 to form a seal therebetween, and be made of a material that passes x-rays 16 without significant attenuation thereof, i.e., an x-ray transmissive material or, as used synonymously herein, a radiolucent material, such as a carbon fiber plastic, polymeric, or other plastic based material.

Figure 4:
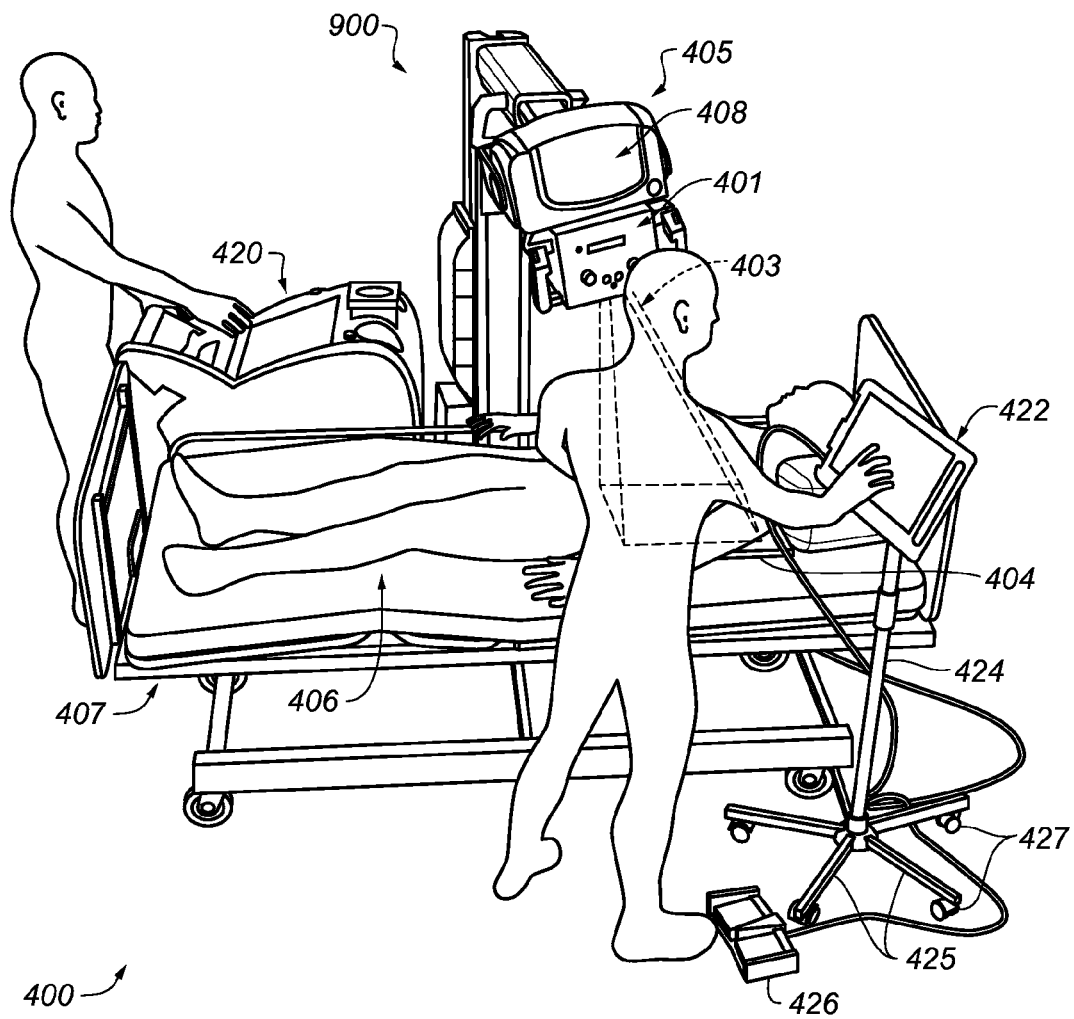
FIG. 4 is a perspective view of an exemplary bedside mobile digital radiographic (DR) dynamic imaging system in use.

FIG. 4 is a perspective view of a mobile digital radiographic (DR) imaging system 400 that may include: a processing console 420, embodied as a wheeled mobile x-ray cart 900 (FIG. 9) having a processing system with electronic memory therein, a generally planar DR detector 404 similar in construction to the DR detector 40 described above, an x-ray source 408 configured to generate radiographic energy, a collimator 401 to shape the x-ray beam 403 emitted by source 408, and a digital monitor 422 configured to display radiographic and fluoroscopic images captured by the DR detector 404, according to one embodiment. The processing console 420 may also include a digital monitor thereon similar in operation to the digital monitor 422. The DR detector 404 may include a two dimensional array 12 of addressable photosensitive cells 22 (pixels) as described herein above. The DR detector 404 may be positioned to receive a collimated x-ray beam 403 passing through a patient 406 lying on a bed 407 during a radiographic fluoroscopy session. As shown in FIG. 4, the mobile radiographic imaging system 400 may use an x-ray source 408 that emits collimated x-rays, e.g. an x-ray beam 403, selectively aimed at and passing through a preselected region of the subject 406. The DR detector 404 is positioned underneath patient 406 in a perpendicular relation, as much as possible, to a substantially central ray of the x-ray beam 403. The location of particular pixels in detector 404 may be recorded according to column and row as described herein, in order to determine a distance between selected ones of the pixels. The density of pixels in a particular DR detector is known. For example, the pixel density may include any one designed pixel density selected from a range of between about ten pixels per millimeter to about twenty pixels per millimeter in one or both rectilinear (column×row) dimensions of the planar DR detector 404.

The photosensitive cells of detector are read-out by digital image processing electronics described herein to be eventually displayed on the digital monitor 422 for viewing during a fluoroscopic imaging session. The read out electronics may communicate with a processing console 420 over a wireless transmitter to transmit fluoroscopic image data thereto. The processing console 420 includes a processing system having electronic memory and may also be used to control the x-ray source 408, the aperture size and shape of the electronic collimator 401, a projection angle of the x-ray beam 403 relative to the tube head 405 by manipulating the electronic collimator aperture, the tube head 405 electric current magnitude, and thus the fluence of x-rays in x-ray beam 403, and thus the energy level of the x-ray beam 403. The processing console 420 may transmit images and other data to the connected digital monitor 422 for display thereon. The processing system of processing console 420 may also be used to selectively identify pixels in the array by a row×column index for having absorbed a particular amount of radiographic energy, such as a high intensity and energy level, and to record the row and column indices of those pixels for source-to-image distance and tilt calculations, as described herein. A portion or all of the processing console 420 functions may reside in the detector 404 in the on-board processing system 36 as described herein.

DR detector 404 may include a three-dimensional, or three-axis, inclinometer, which may be referred to herein as an accelerometer, inertial sensor, or tilt sensor. In one embodiment, the DR detector 404 may be configured to transmit its three-dimensional tilt coordinates to the processing console 420. In one embodiment, the DR detector 404 may be configured to receive three-dimensional tilt coordinates transmitted from the collimator 401, which may include its own separate three-dimensional inclinometer. In one embodiment, both the DR detector 404 and the collimator 401 may be configured to transmit their three-dimensional tilt coordinates to the processing console 420. The recipient of the three-dimensional tilt coordinates, the processing console 420 or the DR detector 404, may be configured to calculate a respective planar positions of the DR detector 404 and the collimator 401 to determine an angular displacement of the DR detector 404 and/or the collimator 401 relative to a parallel orientation thereof. The angular displacement so determined may be displayed on the monitor 422, which displacement may include a calculated displacement having a zero value which indicates that the collimator 401 and the detector 404 are disposed parallel to each other. The angular displacement may include a calculated displacement having a 30° value which indicates that the collimator 401 and the detector 404 are displaced from a parallel orientation by 30°.

The x-ray source 408 and collimator 401 taken together may be referred to herein as a tube head 405. The collimator 401 may include an electronic collimator 401 that is configured to communicate wirelessly with the detector 404 or with the processing console 420. The collimator 401 may communicate three-dimensional coordinates as determined by its connected inclinometer. The collimator 401 may communicate positions of the collimator blades that shape its aperture, such as width and length dimensions of the collimator aperture, for example. As described herein, the collimator 401 may include a three-dimensional inclinometer configured to dynamically transmit measured three-dimensional tilt coordinates to the detector 404 and/or to the processing console 420. Collimator blades contained in the electronic collimator 401 control a shape and size of an aperture of the collimator and, thereby, an exposure area on the detector 404, which exposure area receives x-rays of the x-ray beam 403 generated and emitted by the x-ray source 408. The pixels in the exposure area, or radiation field, transition to a charged state upon receiving x-ray radiation. The collimator blades may be configured as a pair of parallel blades forming a rectangular aperture, which blades may be individually adjustable under programmed motor control. Control instructions for adjusting the electronic collimator aperture 501 may be transmitted from the processing console 420, which may also receive positioning feedback data from the collimator 401 indicating precise height and width dimensions of the electronic collimator aperture 501, which precise height and width dimensions may then be numerically displayed on the digital display monitor 422. The wheeled mobile cart containing processing console 420 may be used together with the display monitor 422 supported by a lightweight stand 424. Wheels 427 may be attached to the lightweight stand 424 via a plurality of stabilizing legs 425 for rolling the stand 424 across a surface, such as a floor, together with the processing console 420. A foot pedal assembly 426 having one or more pedals may be configured to initiate and terminate serial radiographic image acquisition (fluoroscopy). The foot pedal assembly 426 may also be configured as to switch the mobile radiographic imaging system 400 into alternate radiographic operating modes, such as between a fluoroscopic imaging mode and a standard single image projection radiography mode.

Figure 5:
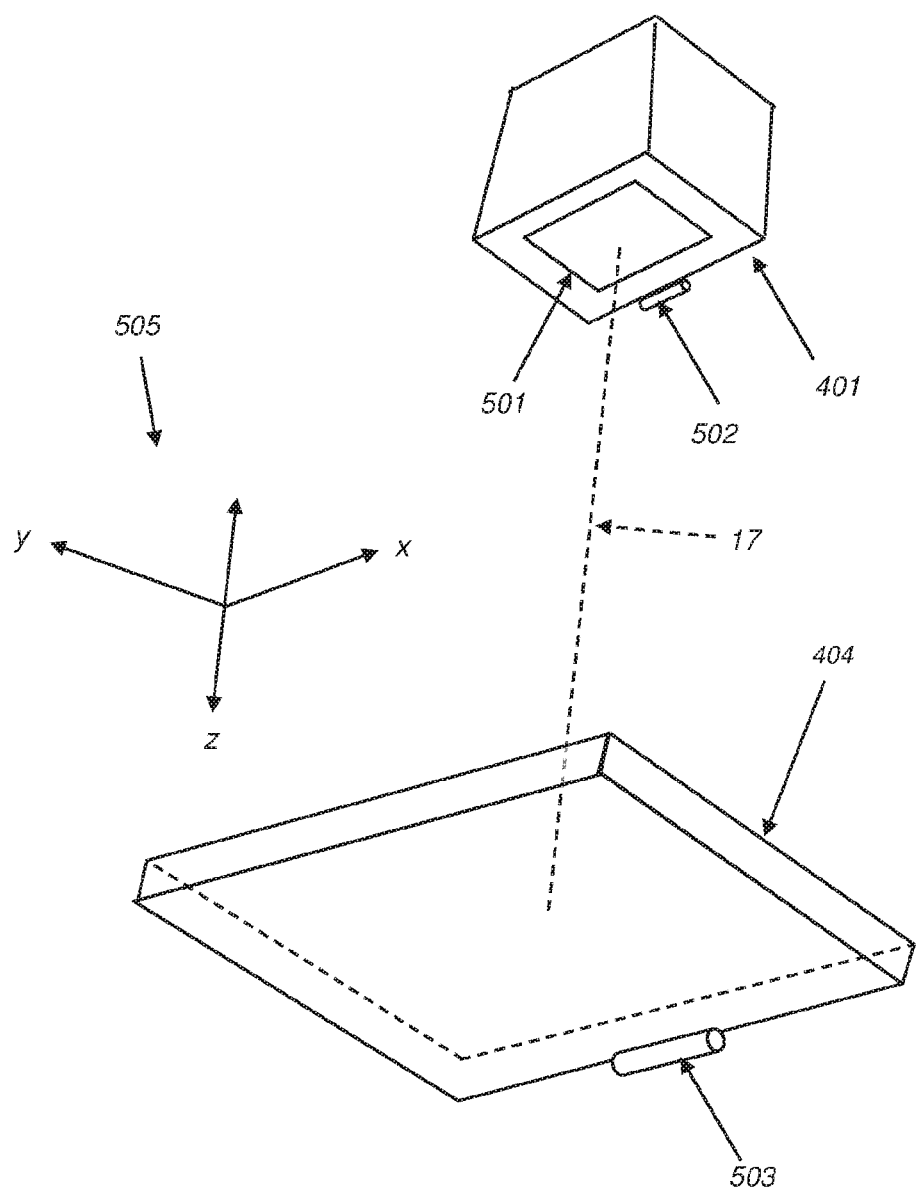
FIG. 5 is a perspective view of a collimator and DR detector alignment system.

FIG. 5 illustrates an exemplary configuration of an electronic collimator 401 having a rectangular aperture 501 and a three-dimensional inclinometer 502. The collimator 401 is arranged in a spatial relationship with DR detector 404 having its own three-dimensional inclinometer 503, which spatial relationship may represent the spatial arrangement of the collimator 401 and DR detector 404 as illustrated in the mobile radiographic imaging system 400 of FIG. 4. The three-dimensional inclinometers 502, 503, may generate and transmit data, as described herein, identifying their spatial orientation with respect to three dimensional coordinates 505. Such three-dimensional coordinate data may be used to calculate an angular value identifying a displacement of the collimator 401 and DR detector 404 away from a parallel orientation therebetween, whereby a parallel orientation may be represented by an angular displacement value of 0°. In particular, an angular displacement of 0° may also be interpreted to indicate that a substantially central ray 17 of an x-ray beam collimated by collimator 401 impacts the imaging array of detector 404 at an angle close to about 90°, i.e., the central ray 17 is perpendicular to a surface of the DR detector 404. The angular displacement value may be interpreted as generally pertaining to planes occupied by a plane of the planar detector 404 and to the plane occupied by the rectangular aperture 501 of the collimator 401.

Figure 6A:
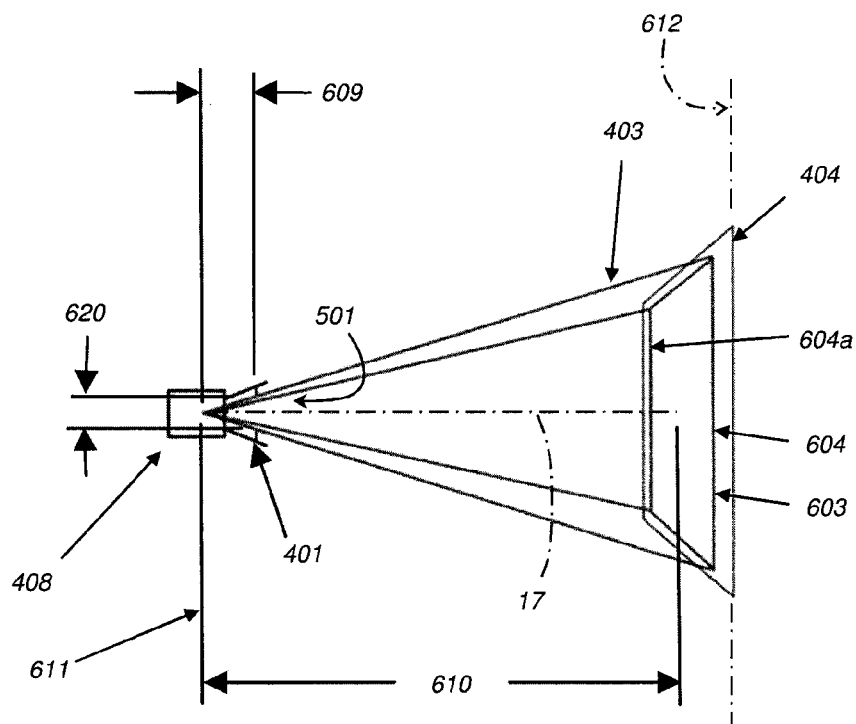
FIGS. 6A-6B is a perspective diagram of an exemplary radiographic imaging system.
Figure 6B:
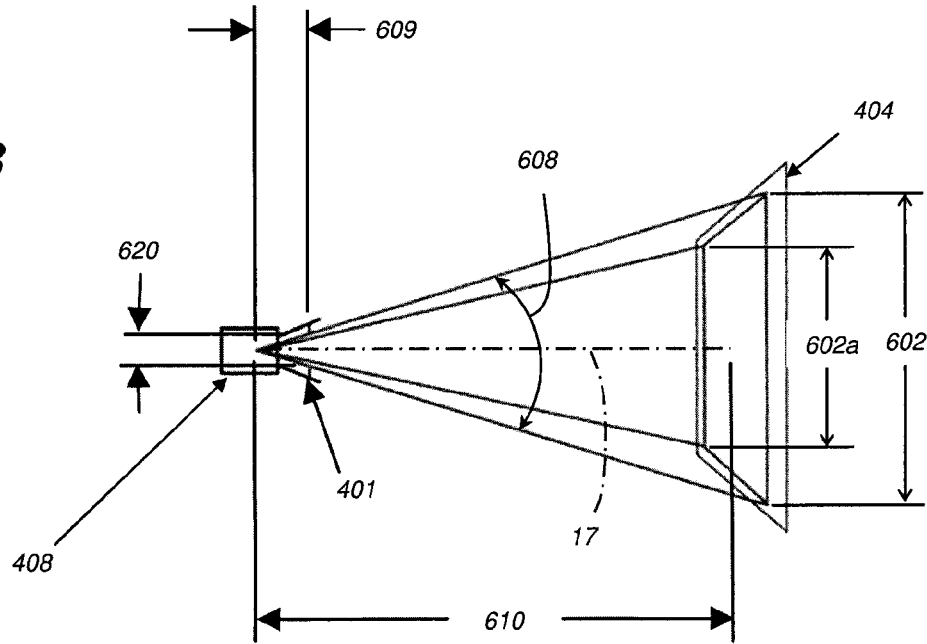
Figure 6C:
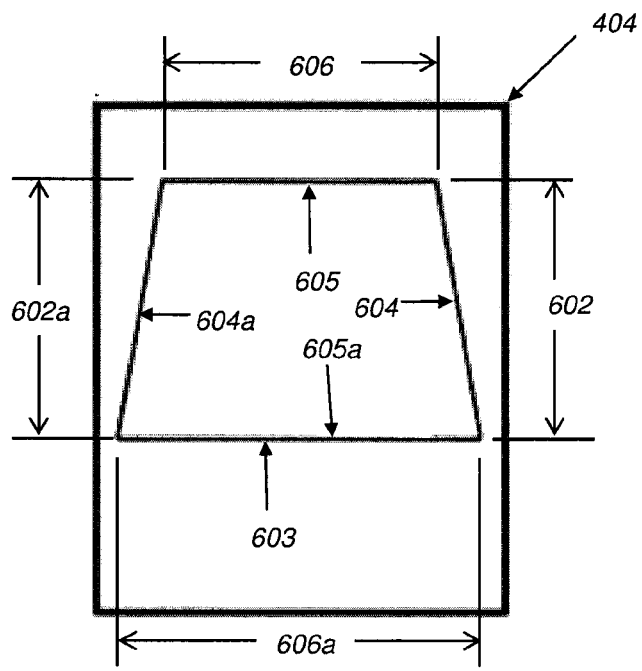
FIGS. 6C-6D are front view diagrams of a radiation field on a DR detector.
Figure 6D:
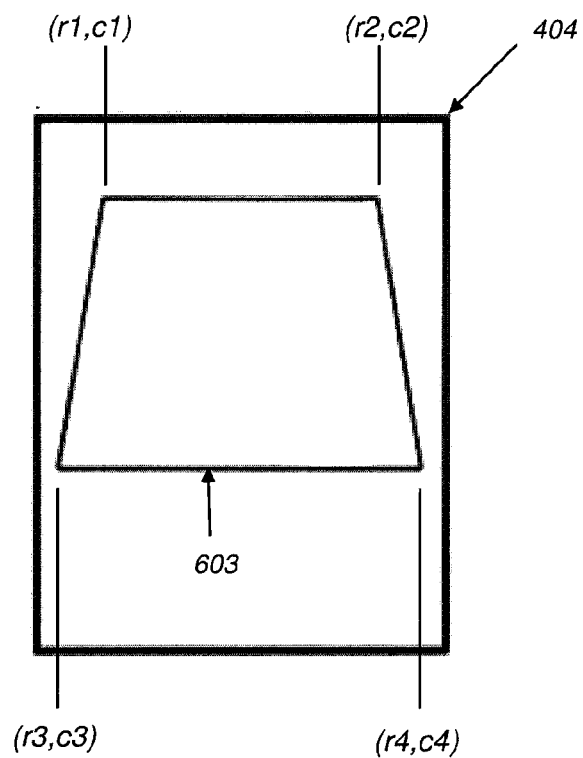

FIGS. 6A-B are schematic perspective diagrams of the mobile radiographic imaging system 400 of FIG. 4 illustrating the x-ray source 408 emitting a collimated x-ray beam 403 toward a DR detector 404. FIGS. 6C and 6D are front views of the radiation field 603 created by the collimated x-ray beam 403 impacting the DR detector 404. The shape and size of the radiation field 603 is controlled by manipulating the electronic collimator 401, in particular, the aperture 501 (FIG. 5) thereof. As disclosed herein, the electronic collimator 401 is configured to wirelessly transmit and receive three-dimensional coordinate data to and from the detector 404, and/or to the processing console 420, which coordinate data is used to identify their respective spatial orientations. The electronic collimator aperture 501 includes a known and adjustable height, or vertical dimension, 620 which determines a height or vertical dimension 602 and 602a of the sides 604, 604a, respectively, of the radiation field 603 on the DR detector 404. The vertical dimension of the collimator aperture 501 may be adjusted by increasing or decreasing a gap size between one pair of horizontal parallel collimator blades, such as by electronically controlling an electric motor drive therefor. Similarly, the electronic collimator aperture 501 includes a known and adjustable width, or horizontal dimension (not shown), which determines, as illustrated in FIG. 6C, a width or horizontal dimension 606 and 606a of the sides 605, 605a, respectively, of the radiation field 603 on the DR detector 404. The horizontal dimension of the collimator aperture 501 may be adjusted by increasing or decreasing a gap size between one pair of parallel vertical collimator blades, such as by electronically controlling a motor drive therefor. The precise dimensions (height, width) of the current collimator aperture 501 may be numerically displayed on the digital monitor 422.

The tube head 405 containing the x-ray source 408 and collimator 401 may be precisely fabricated such that a collimation distance 609 between the focal spot of the x-ray source 408 and the plane of the electronic collimator aperture 501 is known precisely. Also, the focal spot of the x-ray source 408 may be selectively positioned so that a central ray 17 thereof passes orthogonally through the plane of the electronic collimator aperture 501 at a center thereof. This allows a determination of the vertical angle 608 between the upper and lower edges of the vertical span of the x-ray beam 403 which angle 608 may assume to be bisected by the central ray 17 as illustrated in FIG. 6B. Similarly, this allows a determination of the horizontal angle (not shown) between the left and right edges of the horizontal span of the x-ray beam 403 which horizontal angle may assume to be bisected by the central ray 17. These known distances, angles and dimensions just described may be stored in electronic memory for use by the processing system of the processing console 420 to calculate a SID and tilt angle of the plane of DR detector 404 relative to the plane of the collimator aperture 501, as described herein. In one embodiment, the distances, angles and dimensions may be transmitted to the detector 404 for use by on-board processing system 36 of the DR detector 404 to calculate a SID and tilt angle of the plane of DR detector 404 relative to the plane of the collimator aperture 501, as described herein.

As illustrated in FIG. 6C, the shape of the radiation field 603 does not have the same proportions as the rectangular electronic collimator aperture 501 because the DR detector, in this example, is not oriented in a plane parallel to the plane of the electronic collimator aperture 501. The shape of the radiation field of FIG. 6C may be described as trapezoidal which indicates that the DR detector 404 is tilted along one of its orthogonal axes (height or width) relative to the electronic collimator aperture 501. However, the radiation field 603 may assume various trapezoidal or other shapes depending on the relative spatial orientations of the plane occupied by the DR detector 404 and the plane occupied by the electronic collimator aperture 501. The shape of the radiation field may be shaped to have four unequal sides depending on the relative orientations of the DR detector 404 and the electronic collimator aperture 501. The electronic collimator blades may be adjusted to control a size of the aperture 501 using manual control knobs placed on the collimator 401 or on another suitable location of the mobile radiographic imaging system 400, such as on the processing console 420. The electronic collimator blades may be adjusted using touch screen controls on the digital monitor 422 or on the digital monitor in the processing console 420. The electronic collimator blades may also be adjusted by automatic program control residing in the processing console 420, for example.

As illustrated in FIG. 6D, the pixels of DR detector 404 corresponding to four corners (r1, c1), (r2, c2), (r3, c3) and (r4, c4) of the trapezoidal radiation field 603 may be detected by capturing a frame of radiographic image data in DR detector 404 using the outputs of the read out electronics to detect intensity or brightness differences, i.e., charge state transitions, in the DR detector pixels along edges 604, 604a, 605, 605a, of the radiation field 603. The four corners of the trapezoidal radiation field 603 provide row coordinates r1, r2, r3, and r4, and column coordinates c1, c2, c3, and c4 of the radiation field. Thus, using programmed Cartesian functions the length dimensions 606, 606a, 602 and 602a may be numerically calculated by the processing system of the processing console 420 and/or the DR detector 404 using the four corner coordinates (r1, c1), (r2, c2), (r3, c3) and (r4, c4) as Cartesian coordinates in combination with the known pixel density of DR detector 404. Similarly, using simple programmed trigonometric functions the SID 610 and tilt angle—between the plane 611 of the x-ray source focal point (presumed to be orthogonal to a central ray 17 of the x-ray beam 403) and the plane 612 occupied by the DR detector 404—may be calculated by the processing system of the processing console 420 and/or the DR detector 404 using the known distance 609 between the x-ray source focal point and the plane of the electronic collimator aperture 501, the height and width dimensions of the electronic collimator aperture 501, which distance 609 and electronic collimator aperture 501 dimensions also allow derivation of the magnitude of the angle 608, and the calculated dimensions 606, 606a, 602 and 602a. In the exemplary configuration of FIGS. 6C and 6D, simple programmed trigonometric calculations using the detected four corner coordinates (r1, c1), (r2, c2), (r3, c3) and (r4, c4) may determine that sides 605 and 605a are parallel, or, if not parallel, their angular displacement, the lengths of the sides 604, 604a, 605, and 605a, and the interior angles of the four corners of the trapezoidal radiation field 603. Parallelism may be determined, for example, if the detected row coordinates r1, r2, are equivalent or deviate within an acceptably small margin. Similarly, parallelism in an orthogonal direction (height or width) may be determined, for example, if the detected column coordinates c1, c3, are equivalent or deviate within an acceptably small margin. The row coordinates r(x) may begin at one edge having a value of zero r0 up to a maximum row coordinate corresponding to a row number at an opposite edge of the DR detector 404. Similarly, the column coordinates c(x) may begin at one edge having a value of zero c0 up to a maximum column coordinate corresponding to a column number at an opposite edge of the DR detector 404. As an example, the row, column coordinates (r3, c3) and (r4, c4) may be used to calculate a distance of the terminal points of trapezoid edge 605a from the nearest edges of the imaging area array of DR detector 404. This calculation may be used to provide a marginal size of a possible radiation field increase to be implemented by increasing a size of the collimator aperture 501, as described herein.

Figure 7A:
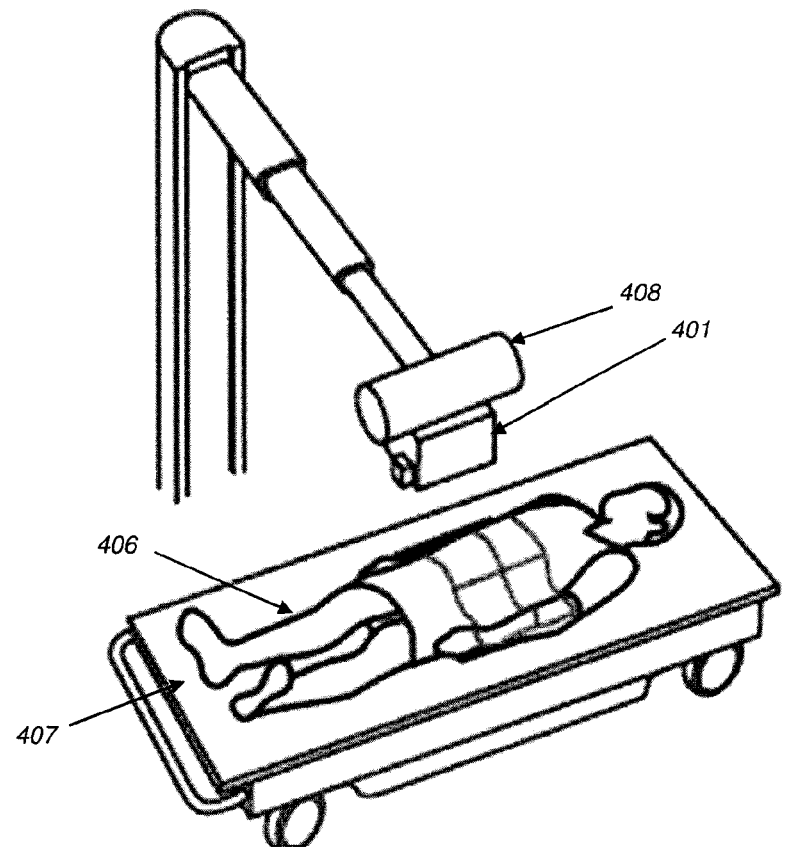
FIG. 7A is a view of a collimator filter pattern projected onto a patient and DR detector.
Figure 7B:
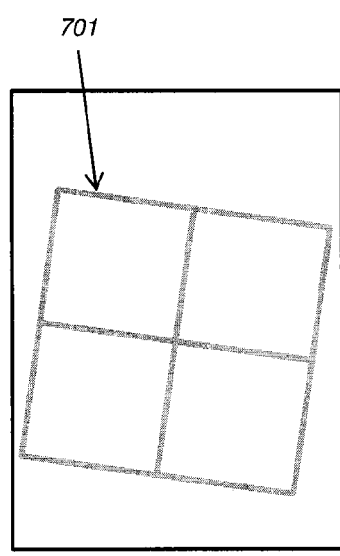
FIGS. 7B-7C are diagrams of exemplary collimator filter patterns.
Figure 7C:
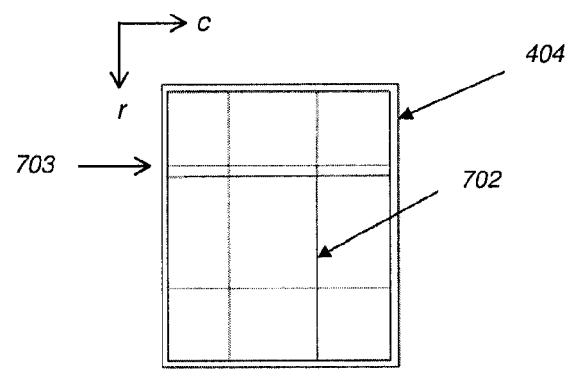

FIGS. 7A-7C illustrate radiographic projection patterns that may be used with the radiographic imaging system 400 of FIG. 4. A patient 406 is positioned on a bed 407 having DR detector 404 (not visible in FIG. 7A) placed beneath the patient. A radiographic scout image may be captured by DR detector 404 using x-ray source 408 and electronic collimator 401, wherein a collimator filter having the cross-haired shape 701 is positioned in the collimator to be radiographically projected onto the DR detector 404. The cross-haired filter pattern 701 may be generated by selectively placing radiopaque metal wires in a filtering position in the electronic collimator 401, for example. Using detected row and column coordinates r, C of the corners or other features of the cross-hair pattern 701, corresponding to pixels of the DR detector 404, similar to the four corner coordinates (r1, c1), (r2, c2), (r3, c3) and (r4, c4), described hereinabove, the angular rotational position of the rectangular DR detector 404 relative to the rectangular electronic collimator aperture 501, as represented by the cross-hair filter pattern 701, can be determined. Referring to the exemplary configuration of FIG. 7B, the rotational position of the rectangular DR detector 404 relative to the rectangular electronic collimator aperture 501 is displaced, which angular displacement may be calculated, based on the determined row and column coordinates, using simple programmed trigonometric functions described hereinabove. FIG. 7C illustrates an example filter pattern 702, that may be used in the electronic collimator 401, having an asymmetrical feature of closely spaced parallel lines 703, which may be detected and used by the radiographic imaging system 400 to assist in distinguishing length and width dimensions of the DR detector 404 relative to the length and width dimensions of the electronic collimator aperture 501. It will be understood that the collimator filter patterns illustrated in FIGS. 7B-7C are exemplary, and various filter patterns may be configured for use in the embodiments described herein. Although a size of the filter pattern 701 relative to a size of the detector 404 is substantial, as depicted in FIG. 7B for ease of illustration, an actual size of the filter pattern 701, or scout image, may range from about one (1) inch on a side to about twelve (12) inches on a side. In one embodiment, an actual size of the filter pattern 701, or scout image, may range from about one inch to about three inches on a side. The filter pattern 701 may be electromechanically moved out of the path of the x-ray beam 403 within the collimator 401 prior to initiating a fluoroscopic examination or, if the scout image so captured is used for diagnostic purposes, the scout image may be digitally processed using image processing software designed to remove artifacts generated therein by the filter pattern 701.

Figure 8:
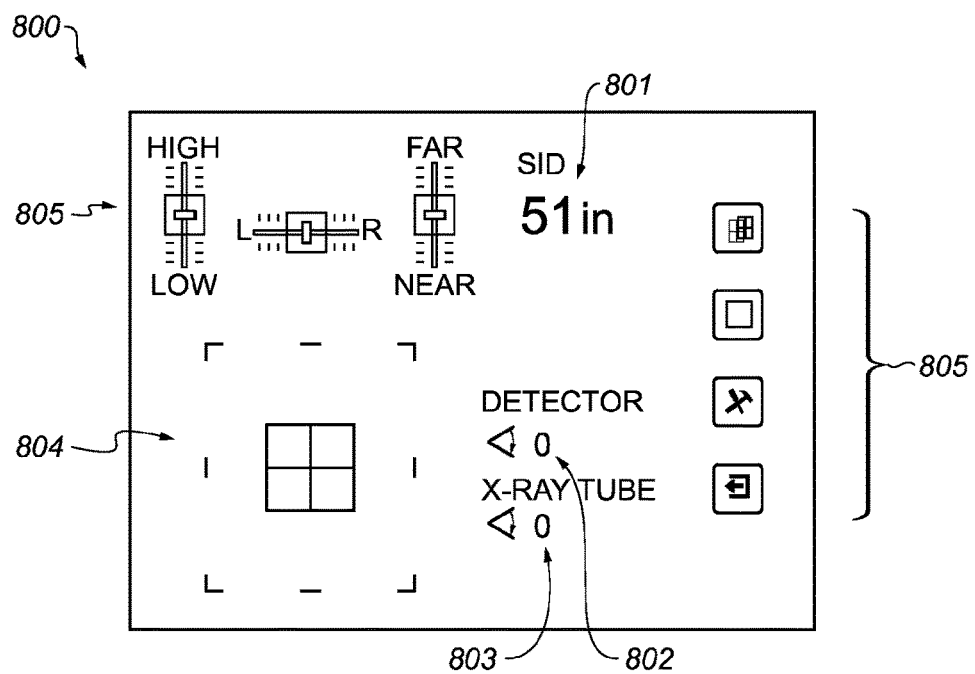
FIG. 8 is a diagram of an exemplary digital monitor display.

FIG. 8 illustrates an exemplary configuration of a display 800 which may be presented on digital monitor 422. The digital monitor may be used to display a calculated SID 801, as illustrated, as well as a calculated relative detector tilt angle 802, detector rotation angle 803, a captured radiographic image 804 depicting an imaged collimator filter pattern placement, as well as a graphical user interface 805 for operator use to control different functions of the mobile radiographic imaging system 400. As described herein, other numerical data fields may be provided on the display 800. The exemplary display configuration of FIG. 8 may be a part of a touch screen implementation for operator control of the mobile radiographic imaging system 400, or it may be configured as a status display wherein control devices, such as knobs, keyboards, mouse, buttons, etc., of the mobile radiographic imaging system 400 may be positioned on other components thereof.

Figure 9:
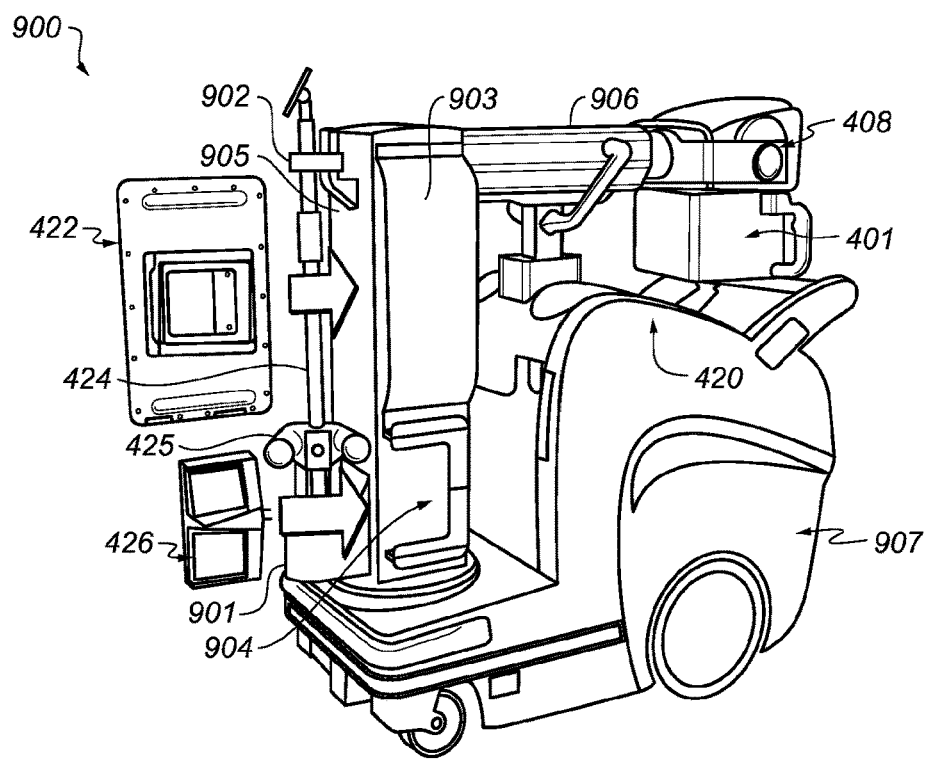
FIG. 9 is a perspective view of the exemplary bedside mobile digital radiographic (DR) dynamic imaging system of FIG. 4 in a stowed configuration.

FIG. 9 is a perspective view of the wheeled mobile x-ray cart 900 of the mobile digital radiographic imaging system 400. FIG. 9 depicts the major components of the mobile radiographic imaging system 400 in their stowed positions on the wheeled mobile x-ray cart 900 which are configured for rollably transporting the mobile radiographic imaging system 400 in a patient care facility. A major advantage of the mobile radiographic imaging system 400 is that serial radiography (e.g., fluoroscopy) becomes completely mobile in nature because the necessary components are easily transportable to a patient bedside using the wheeled mobile x-ray cart 900. When it is desired for the mobile radiographic imaging system 400 to be used for general purpose radiography, the hardware described herein for serial radiography may be used for general purpose imaging. As shown in FIG. 9, a storage nest 901 is configured to store the lightweight stand 424. A feature of the stand 424 is that the stabilization legs 425 can be folded to minimize required space for transport, and storage nest 901 is configured to receive the legs 425 in a folded state. An upper restraint 902 has a nesting feature assembly sized to receive the pole of the stand 424 and includes a flexible strap to secure it. Monitor storage 903 is used to secure the digital display 422 during transport. The digital display 422 may be inserted into the monitor storage 903 in the direction indicated by the corresponding arrow. Monitor storage 903 is formed as a continuous and rounded shape such that it does not snag or inhibit movement of high voltage cables that may drape along the mobile radiographic imaging system 400. Foot pedal assembly storage 904 is used to secure the foot pedal assembly 426 during transport. The foot pedal assembly 426 may be inserted into the foot pedal assembly storage 904 in the direction indicated by the corresponding arrow. A feature of the foot pedal assembly 426 is an external groove configured to receive its connectivity cable before insertion into the foot pedal assembly storage 904. The bottom of the vertical support column 905 is attached to, and is rotatable relative to, the wheeled transport frame 907 which contains the processing console 420. The tube head comprising x-ray source 408 and electronic collimator 401 is attached to one end of a horizontal boom 906 which, in turn, is attached to a top end of the vertical support column 905. The tube head is configured to be movable to a variety of angular positions with respect to horizontal boom 906.

In one embodiment of a method of using the mobile radiographic imaging system 400, an operator may position a patient 406 on a bed 407 as illustrated in FIG. 7A, and place a DR detector 404 beneath the patient 406 in a position orthogonal to an x-ray beam to be emitted by x-ray source 408, or as close to an orthogonal position as desired. In one embodiment, a collimator light may be activated and used by the operator to determine a size and position of the radiation field on the patient 407. In one embodiment, the three-dimensional inclinometers 502, 503, in the collimator 401 and the DR detector 404 may be used to assist in placing the detector close to the parallel position by transmitting their detected spatial orientations to the processing console 420 which may be used to calculate a numerical displacement angle representing a magnitude of deviation from parallel, which may then be displayed on the digital monitor 422 for use by the operator during manual positioning of the DR detector 404. In one embodiment, the three-dimensional inclinometers 502, 503, in the collimator 401 and the DR detector 404, and their parallel displacement deviation as displayed on the digital monitor 422, are used by the operator to position the DR detector 404 in a parallel position relative to the plane of the electronic collimator aperture 501 within a selected tolerance so that no trapezoidal radiation field 603 is generated on the DR detector 404, rather, a rectangular radiation field is generated.

A scout image may then be captured in the DR detector 404. In one embodiment, as depicted in FIG. 7A, a collimator filter pattern 701 may be used for the scout image capture, for example. In one embodiment, after positioning the DR detector 404 beneath patient 406, and prior to the scout image being captured, the operator may enter an approximate SID value, as determined by the operator using a visual approximation, by entering the estimated SID into processing console 420 so that its processing system may calculate a selected size of the electronic collimator aperture 501 to generate a preferred (estimated) size for the scout image radiation field. The radiation field 603 thus captured may be used to calculate an actual size of the radiation field 603, for example, as described herein, and a trapezoid edge such as edge 605a depicted in FIG. 6C may be calculated as to its actual length and position relative to edges of the detector 404. The method may further comprise determining an amount that the radiation field 603 may be increased without exceeding the edges of the DR detector 404, that is, an amount that the edge 605a of trapezoid radiation field 603 may be increased so as to entirely contain the radiation field 603 within the imaging area of the DR detector 404. Edge 605a is illustrated as an example herein, because its terminal points are closest to edges of the DR detector 404, however, other dimensions of the radiation field 603 may also be used to calculate a maximum size of the radiation field 603 accordingly. If the inclinometers are used to position the DR detector in a parallel orientation to the collimator aperture, then a rectangular radiation field may be generated on the DR detector and used to calculate a marginal increase amount for the collimator aperture so that the radiation field may be maximized and still be contained within the borders of the DR detector.

After determining an amount that the radiation field 603 may be increased without exceeding the edges of the DR detector 404, the programmed trigonometric functions may be used to calculate an increase in the size of the electronic collimator aperture 501 corresponding to the amount of increase determined for the size of the radiation field 603. The electronic collimator aperture 501 may then be increased by controllably adjusting a position of the collimator blades accordingly. After the collimator blades are repositioned as calculated, the three-dimensional inclinometers 502, 503, in the collimator 401 and the DR detector 404, respectively, are monitored to detect movement thereof. So long as no movement is detected thereby, fluoroscopic examination may begin and may be maintained as long as desired, using the DR detector 404 for capturing fluoroscopic images of the patient 406 using the determined maximum radiation field 603. The fluoroscopic images may be viewed on digital display 422. The collimator 401 and DR detector 404 are preferably fixed in their respective positions after acquiring the scout image (or images) so as to insure that the radiation field 603 is not moved off the imaging area of the DR detector 404. In one embodiment, after a maximum size of the radiation field 603 is determined and the electronic collimator aperture 501 is adjusted accordingly, the operator may activate a collimator light to illuminate the expected radiation field on the patient. The operator may then selectively manually shrink the maximum radiation field according to requirements of the examination being performed or for an added margin of safety. In one embodiment, after reducing a size of the expected radiation field, the operator may optionally capture another scout image. The scout images thus captured may be stored and used for diagnostic purposes, or may be discarded.

The calculations described herein according to trigonometric functions are well known by those having ordinary skill in the art and are not described herein in detail. One example trigonometric relationship includes: (SID÷height of collimator aperture)=(focal point to collimator aperture distance÷height of radiation field). The SID may be measured from the focal point to the center of the radiation field on the DR detector 404 along a central ray 17 and assumes symmetric perpendicular centered collimation as described herein. An angle of incidence, i.e., a tilt angle between central ray 17 and the plane of the DR detector 404 can be determined by the ratio of the length of the long side 605a to the short side 605 of the trapezoid radiation field 603. As described herein, the collimator blade positions controlling a size of the electronic collimator aperture 501 provide information on the total angle 608 of the emitted x-ray beam 403 to determine if perpendicularity with the DR detector 404 is within acceptable limits. If it is determined that the radiation field 603 may be exceeding the edges of the DR detector 404, such as by excessive detected movement using three-dimensional inclinometers 502, 503, a warning text message may be displayed on the digital monitor 422, a warning sound may be generated using a speaker controlled by processing console 420, a termination of the fluoroscopic imaging session may be forced by powering down the x-ray source, the electronic collimator aperture may be automatically reduced, or other safety procedures and/or mechanisms may be triggered.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "service," "circuit," "circuitry," "module," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to methods of operating the mobile radiographic imaging system 400. It will be understood that these methods can be partially or wholly implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified herein.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A method of operating a mobile fluoroscopic imaging system comprising a mounted x-ray source, a collimator attached to the x-ray source, and a freely positionable DR detector mechanically unconnected to the x-ray source and the collimator, the method comprising:
   positioning the x-ray source and the DR detector about a patient;
   storing data defining a distance between a focal spot of the x-ray source and a plane occupied by the collimator along a line perpendicular to the plane occupied by the collimator, and a size of an aperture of the collimator; and
   determining a source-to-image distance and tilt angle of the x-ray source relative to the DR detector including:
      activating the x-ray source and capturing a scout image in the DR detector;
      calculating dimensions of the scout image; and
      determining the source-to-image distance and the tilt angle based on the data defining the distance between the focal spot of the x-ray source and the plane occupied by the collimator, the size of the aperture of the collimator and on the dimensions of the scout image.

2. The method of claim 1, further comprising:
   attaching a first inclinometer to the DR detector;
   attaching a second inclinometer to the collimator;
   generating and transmitting three-dimensional orientation signals associated with spatial orientations of the x-ray source and the DR detector using the first and second inclinometers;
   calculating a relative spatial displacement as between the x-ray source and the DR detector based on the three-dimensional orientation signals; and
   displaying a numerical value of the angular displacement.

3. The method of claim 2, further comprising determining a magnitude of deviation from a parallel orientation as between the x-ray source and the DR detector using the orientation signals.

4. The method of claim 1, further comprising manually adjusting the aperture of the collimator to a size that is known to generate a radiation field to fit within borders of the DR detector.

5. The method of claim 1, further comprising the collimator automatically electromechanically adjusting an aperture of the collimator to a size that is known to generate a radiation field to fit within borders of the DR detector.

6. The method of claim 5, further comprising automatically electromechanically adjusting the aperture to generate a radiation field between about one inch and about three inches across on the DR detector.

7. The method of claim 2, further comprising monitoring whether the relative spatial displacement occurs using the first and second inclinometers.

8. The method of claim 7, further comprising increasing a size of the aperture of the collimator such that a radiation field on the DR detector remains within the borders of the DR detector.

9. The method of claim 8, further comprising starting a fluoroscopic examination of the patient using the x-ray source and the DR detector, wherein the system is configured to trigger a warning signal if the relative spatial displacement occurs.

10. The method of claim 1, further comprising placing a patterned filter in the collimator and capturing the scout image in the DR detector having the filter pattern thereon.

11. The method of claim 10, further comprising using the filter pattern to determine a relative orientation of the x-ray source and the DR detector.

12. A mobile radiographic imaging system comprising:
   a wheeled mobile x-ray cart comprising a processing system;
   a tube head comprising an x-ray source and a collimator, the tube head attached to the mobile x-ray cart using a support column;
   a DR detector mechanically unconnected to the tube head; and
   the processing system having stored therein data defining a distance between a focal spot of the x-ray source and a plane occupied by the collimator along a line perpendicular to the plane occupied by the collimator, and data defining a size of an aperture of the collimator,
   wherein the processing system is configured to determine a source-to-image distance and tilt angle of the x-ray source relative to the DR detector based on: dimensions of a radiographic image captured by the DR detector in response to an activation of the x-ray source, the data defining the distance between the focal spot of the x-ray source and the plane occupied by the collimator, and the data defining the size of the aperture of the collimator.

13. The system of claim 12, further comprising:
   a first inclinometer attached to the DR detector configured to transmit three-dimensional orientation signals associated with a spatial orientation of the DR detector; and
   a second inclinometer attached to the collimator configured to transmit three-dimensional orientation signals associated with a spatial orientation of the collimator,
   wherein the processing system is configured to calculate a spatial displacement as between the collimator relative to the DR detector based on the three-dimensional orientation signals transmitted by the first and second inclinometers.

14. The system of claim 13, wherein the collimator comprises motor driven blades configured to electromechanically adjust the aperture of the collimator to a size that is known to generate a radiation field to fit within borders of the DR detector.

15. The system of claim 14, wherein the system is configured to emit a warning signal if the spatial displacement as between the collimator relative to the DR detector exceeds an acceptable limit.

16. The system of claim 15, further comprising a patterned filter in the collimator, wherein the processing system is configured to determine a relative orientation of the x-ray source relative to the DR detector based on a radiographic image of the patterned filter captured by the DR detector in response to an activation of the x-ray source.

* * * * *